(12) United States Patent
Zacharia

(10) Patent No.: US 8,758,013 B2
(45) Date of Patent: Jun. 24, 2014

(54) PROSTHETIC APPARATUS

(75) Inventor: John Zacharia, San Diego, CA (US)

(73) Assignee: Zimmer Dental, Inc., Carlsbad, CA (US)

( * ) Notice: Subject to any disclaimer, the term of this patent is extended or adjusted under 35 U.S.C. 154(b) by 0 days.

(21) Appl. No.: 13/404,145

(22) Filed: Feb. 24, 2012

(65) Prior Publication Data
US 2012/0294839 A1 Nov. 22, 2012

Related U.S. Application Data

(60) Provisional application No. 61/487,105, filed on May 17, 2011.

(51) Int. Cl.
*A61C 8/00* (2006.01)
*A01N 63/00* (2006.01)
*A61F 2/02* (2006.01)

(52) U.S. Cl.
USPC ...... 433/173; 424/93.1; 424/93.4; 424/93.44; 424/93.45; 623/17.17; 623/11.11

(58) Field of Classification Search
CPC ............ A01N 63/00; A61C 8/00; A61F 2/02; A61K 35/32; A61K 35/747; A61K 35/74; A61L 27/54
USPC ............ 623/11.11, 17.17; 433/173, 167, 174, 433/181–183, 191, 193, 201.1; 424/93.1
See application file for complete search history.

(56) References Cited

U.S. PATENT DOCUMENTS

| | | | |
|---|---|---|---|
| 5,282,746 A | * | 2/1994 | Sellers et al. ................. 433/172 |
| 2004/0166102 A1 | * | 8/2004 | Darouiche et al. ......... 424/93.45 |
| 2007/0298377 A1 | * | 12/2007 | Kenealy et al. ............... 433/173 |
| 2010/0249838 A1 | * | 9/2010 | Stopek et al. ................. 606/246 |
| 2010/0304334 A1 | * | 12/2010 | Layton .......................... 433/173 |
| 2012/0039860 A1 | * | 2/2012 | Roughead et al. ......... 424/93.44 |

* cited by examiner

*Primary Examiner* — Jennifer Pitrak McDonald
*Assistant Examiner* — Qing Xu
(74) *Attorney, Agent, or Firm* — Schwegman Lundberg & Woessner, P.A.

(57) ABSTRACT

Prosthetic apparatuses with probiotic microorganisms to control colonization of pathogenic bacteria are disclosed. The prosthetic apparatus may include a first portion having a first mating surface, a second portion having a second mating surface that conforms to the first mating surface, and at least one strain of probiotic microorganisms retained between the first and second mating surfaces prior to implantation of the prosthetic apparatus.

15 Claims, 5 Drawing Sheets

PROSTHETIC APPARATUS

CROSS-REFERENCE TO RELATED APPLICATION

This application claims priority under 35 USC §119 (e) to U.S. Provisional Patent Application Ser. No. 61/487,105 filed on May 17, 2011

FIELD OF THE DISCLOSURE

This disclosure generally relates to prosthetic apparatuses and, more particularly, relates to prosthetic apparatuses with probiotic components to control colonization of harmful bacteria on the prosthetic apparatuses.

BACKGROUND OF THE DISCLOSURE

Prosthetic apparatuses are widely used in medical procedures to restore appearance and/or function of lost or damaged body parts, such as joints, hips, bones, and teeth. One problem associated with prosthetic apparatuses is the colonization of harmful bacteria on the surface of the prosthetic apparatuses, especially between closely fitted components. Such colonization of harmful bacteria may affect proper function of the prosthetic apparatus and may cause infection or other adverse effects to surrounding tissues, requiring removal and replacement of the prosthetic apparatus and timely treatment of the infective or otherwise adverse conditions.

For example, while using dental implants to improve oral function is state-of-the-art, and has proven effective and reliable over the years, crestal bone loss remains a common problem associated with the prosthetic treatment and, over time, may jeopardize the effectiveness the prostheses if it leads to implant mobility and failure. While the exact reason for the crestal bone loss is unknown, it may be caused by biological and/or mechanical conditions surrounding the crestal bone tissue.

Current dental prostheses generally include three components to fully define the artificial tooth root: an implant component, which is placed into the prepared osteotomy; an abutment component, which is an extensory unit installed into the implant; and a fixation screw to interconnect the implant and abutment components. The mating fits among the components are predetermined by design and tolerance, and often leave small gaps, or "microgaps", among mated components despite efforts by manufacturers to reduce such microgaps. The microgap may vary in dimension depending on design (e.g. cement-retained or screw-retained) and loading condition of the dental prostheses. For example, the microgap may be from 5-10 micrometer and sometimes can be as wide as more than 60 micrometers.

Studies have shown that known pathogenic bacteria can attach onto the components of dental prostheses. Upon attachment, the sharp edges and undercuts of the microgap create a shelter for pathogenic bacteria to colonize within the microgap and eventually spread to tissues surrounding the dental prostheses. Further, mechanical stress on the components of the dental prostheses may lead to "pumping" of the pathogenic bacteria out of the microgap to facilitate the spread of the pathogenic bacteria.

Efforts to manage pathogenic colonization of the microgap have been met with limited success. Regular dental hygiene has been proven ineffective, as the microgap is smaller than most brush tips and is often submerged in soft or sensitive tissue. Systemic prophylactics have limited effects in the oral environment, as bacteria tends to rapidly aggregate into protected clusters, reducing the efficacy of traditional medicine and increasing the chance of generating antibiotic-resistant bacteria.

Current attempts to address this problem focus on site specific methods to control bacterial colonization within the microgap. For example, some methods attempt to reduce the microgap through tighter component fits and reduced tolerances. Other methods use prosthetic components that medialize the microgap, creating distance between the microgap and crestal bone. Finally, the dental prosthesis may be designed as a single piece or single stage implant or to have the microgap completely filled with cement. However, those are mechanical solutions that try to address the severity or frequency of the symptoms, not the underlying biological cause.

On the other hand, efforts have been directed toward preventing bacterial colonization in medical devices by the use of antimicrobial agents, such as antibiotics. Various methods have previously been employed to contact or coat the surfaces of medical devices with an antimicrobial agent. For example, one method involves flushing the surfaces of the device with an antimicrobial containing solution. Generally, the flushing technique would require convenient access to the site of bacterial colonization, which may be difficult if the site is blocked by body tissues, such as gums. Moreover, the use of antibiotics may trigger bacterial mutation and lead to antibiotic-resistant bacteria. Finally, bacterial colonization may lead to formation of a protective biofilm (e.g. glycocalyx) around the pathogenic bacteria, which may further limit the access and effectiveness of antibiotics.

Alternatives to traditional antibiotics include the use of chemical coatings to create a bactericidal environment. Copper (Cu) and Silver (Ag) are undergoing investigation as non-selective methods for bacterial resistance. However, these methods can produce free radicals, damaging redox reactions in surrounding tissue, and reduce in effectiveness as the body begins coating the affected surface with proteins.

Probiotic microorganisms are also known in general medical hygiene. For example, compositions containing probiotic microorganisms may be used on human skin or oral cavity to inhibit contamination of pathogenic bacteria. Moreover, probiotic microorganisms may be applied through a spray or cleaning wipe to surfaces such as tables, benches, hospital fixtures, equipment, clothing, and beddings. However, use of probiotic microorganisms in prosthetic apparatuses, especially where biological and mechanical conditions are different from known applications, has not been attempted or suggested.

SUMMARY OF THE DISCLOSURE

In accordance with one aspect of the present disclosure, a prosthetic apparatus is provided. The prosthetic apparatus may include a first portion having a first mating surface, a second portion having a second mating surface that conforms to the first mating surface, and at least one strain of probiotic microorganisms retained between the first and second mating surfaces prior to implantation of the prosthetic apparatus.

In accordance with another aspect of the present disclosure, a dental prosthetic apparatus is provided. The dental prosthetic apparatus may include an anchoring member including a center bore having an interior abutting surface, and an abutment member including a base matably received in the center bore of the anchoring member. The base of the abutment member may include an exterior abutting surface that conforms to the interior abutting surface of the anchoring member. The dental prosthetic apparatus may further include at least one strain of probiotic microorganisms retained between the exterior abutting surface of the abutment member and the interior abutting surface of the anchoring member prior to implantation of the dental prosthetic apparatus.

In according with yet another aspect of the present disclosure, a probiotic film for use in a prosthetic apparatus is provided. The probiotic film may include a polymer matrix and at least one strain of microorganisms supported by the polymer matrix.

These and other aspects and features of the disclosure will be better understood upon reading the following detailed description in conjunction with the accompanying drawings.

BRIEF DESCRIPTION OF THE DRAWINGS

For a more complete understanding of the disclosed prosthetic apparatus and method of use thereof, reference should be made to the embodiments illustrated in greater detail in the accompanying drawings, wherein.

It should be understood that the drawings are not necessarily to scale and that the disclosed embodiments are sometimes illustrated diagrammatically and in partial views. In certain instances, details which are not necessary for an understanding of the disclosed apparatus or method which render other details difficult to perceive may have been omitted. It should be understood, of course, that this disclosure is not limited to the particular embodiments illustrated herein.

DETAILED DESCRIPTION OF THE DISCLOSURE

Figure 1:
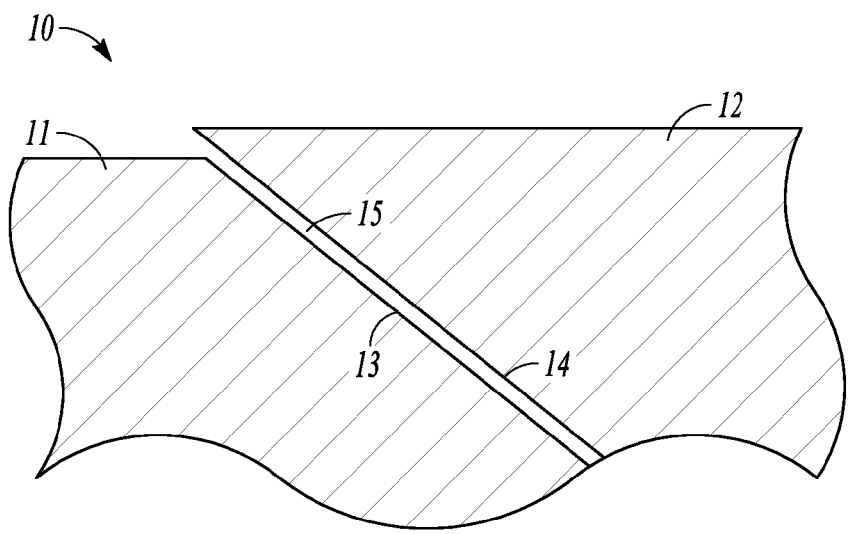
FIG. 1 is an enlarged, fragmentary, and cross-sectional view of a general prosthetic apparatus according to one aspect of the present disclosure, particularly illustrating the microgap between two mated components.

Referring now to the drawings, and with specific reference to FIG. 1, a prosthetic apparatus according to one aspect of the present disclosure is generally referred to by reference numeral 10. The prosthetic apparatus 10 includes a first portion 11 mated with a second portion 12. To that end, the first portion 11 includes a first mating surface 13 that conforms to a second mating surface 14 of the second portion 12. The term "conform" as used in the present disclosure refers to a positional relationship in which two surfaces are closely mated to each other and yet still leave a small gap (e.g. microgaps with micrometer scale inter-surface distances) between at least a portion of the two surfaces.

Figure 2:
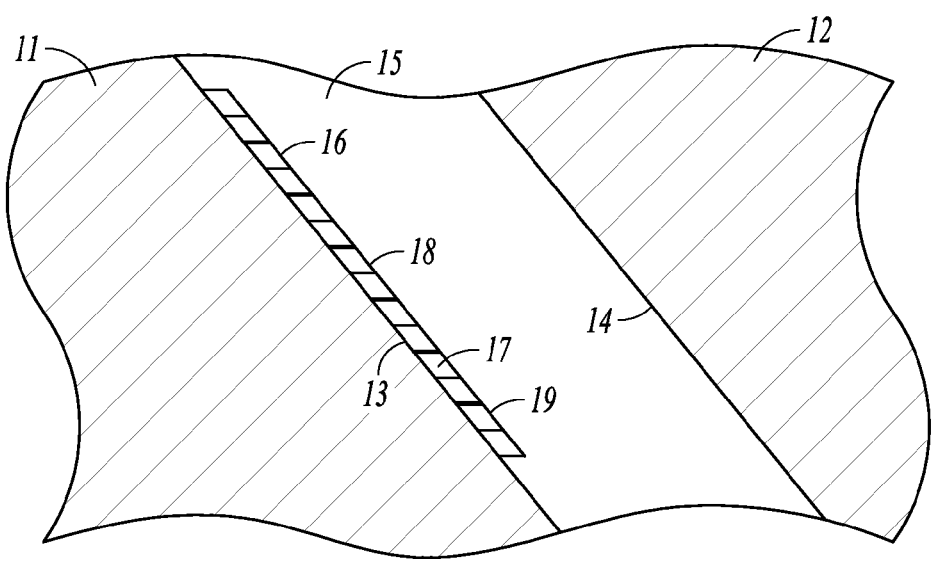
FIG. 2 is an enlarged view of the microgap of the prosthetic apparatus in FIG. 1, particularly illustrating the probiotic microorganisms retained in the microgap.

Turning now to FIG. 2, the space between a portion of the first and second mating surfaces (13, 14) define a microgap 15. The microgap 15 may have an average width of less than 1000 micrometers. In one embodiment, the microgap 15 has an average width of from 5 to 10 micrometers. In another embodiment, the microgap 15 has an average width of no more than 60 micrometers. The prosthetic apparatus 10 further includes at least one strain of probiotic microorganisms 16 retained between the first and second mating surfaces (13, 14) prior to implantation of the prosthetic apparatus 10. The term "retained" as used in the present disclosure refers to a spatial relationship between the probiotic microorganisms and the mating surfaces in which the probiotic microorganisms may or may not be fixed to a specific location, i.e. the probiotic microorganism may migrate from one location to another, but are nevertheless essentially limited to be within the microgap between the mating surfaces at least prior to implantation. As the colonization of the probiotic microorganisms constitute one feature of the present disclosure, the mating surfaces (13, 14) and the microgap 15 may be essentially free of antimicrobial agents. The term "essentially free" as used in the present disclosure means that the amount of antimicrobial agent present in the microgap 15, if at all, should not prevent colonization of the probiotic microorganisms 16 within the microgap 15. For example, the microgap 15 may tolerate an unavoidable amount of residual antimicrobial agent as a result of conventional antibiotic treatment of the oral environment, or as a result of production or sterilization processes of the disclosed prosthetic apparatus.

Still referring to FIG. 2, the at least one strain of probiotic microorganisms 16 may be supported by a polymer matrix 17 to form a probiotic film 18 in some embodiments of the present disclosure. To that end, the probiotic microorganisms 16 may be impregnated in, coated on, or otherwise associated with the polymer matrix 17 prior to implantation of the prosthetic apparatus 10. It is to be understood, of course, that at least some of the probiotic microorganisms 16 may dissociate from the polymer matrix 17 and migrate to other locations within the microgap 15, such as after implantation of the prosthetic apparatus 10. In some cases, at least some of the probiotic microorganisms 16 may even migrate to outside of the microgap 15 after implantation of the prosthetic apparatus 10. Moreover, the use of the polymer matrix 17 to carry the probiotic microorganisms 16 is a non-limiting embodiment of the present disclosure. In other embodiments, the priobiotic microorganism may be directly deposited on one or both of the mating surfaces (13, 14). For example, the probiotic microorganisms 16 can be attached directly to the mating surfaces via embedding in surface roughness, protein adhesion, culturing, or other techniques that do not require a polymer matrix.

The polymer matrix 17 may be made of a non-degradable polymer material in some embodiments. In other embodiments, the polymer matrix 17 may be time-degradable or biodegradable polymer materials. Non-limiting examples of the polymer material for use in the present disclosure may include, but are not limited to, polycaprolactone, polydioxanone, polyglycolide, polyhydroxyalkanoates, polyhydroxybutyrate, poly-3-hydroxybutyrate, poly-4-hydroxybutyrate, polyhydroxyvalerate, polyhydroxyhexnoate, polydroxyoctanoate, polylactic acid, polylactide, poly-L-lactide, poly-DL-lactide, polyvinyl alcohol, Zein, cellulose esters, and applicable copolymers,.

As illustrated in FIG. 2, the polymer matrix 17 may be attached to at least one of the first and second mating surfaces (13, 14). In some embodiments, the polymer matrix 17 may be attached to both of the mating surfaces (13, 14). The polymer matrix 17 may be attached to the mating surfaces (13, 14) through adhesion, chemical bonding, thermal fusion, mechanical attachment or fixation mechanisms, etc. The polymer matrix 17 may also be loosely disposed between the mating surfaces (13, 14) without any attachment thereto. Furthermore, although only one polymer matrix 17 is shown in FIG. 2, the at least one strain of probiotic microorganisms 16 may be supported by more than one polymer matrix 17. For example, the prosthetic apparatus 10 may include two or more polymer matrices 17 either attached to one or both of the mating surfaces (13, 14) or loosely disposed between the mating surfaces (13, 14). The two or more polymer matrices 17 may each support a different strain of probiotic microorganisms or they may each support a blend of probiotic microorganisms.

In some embodiments, the at least one strain of probiotic microorganisms 16 are uncolonized (e.g. dehydrated) prior to implantation, and are capable of colonization in or on the polymer matrix 17, within the microgap 15, and/or on the mating surfaces (13, 14) upon rehydration through contact with body fluid, such as blood and saliva. In other embodiments, the at least one strain of probiotic microorganisms 16 are colonized (e.g. hydrated) in or on the polymer matrix 17, within the microgap 15, and/or on the mating surfaces (13, 14) prior to implantation of the prosthetic apparatus.

In one non-limiting embodiment, colonization of the probiotic microorganisms 16, especially multiple strains of probiotic microorganisms, may lead to formation of a biofilm 19 that hosts or provides support for the probiotic microorganisms 16. For example, the biofilm 19 may be formed of glycocalyx or other extracellular polymer material produced by colonization of the probiotic microorganisms 16.

Figure 3:
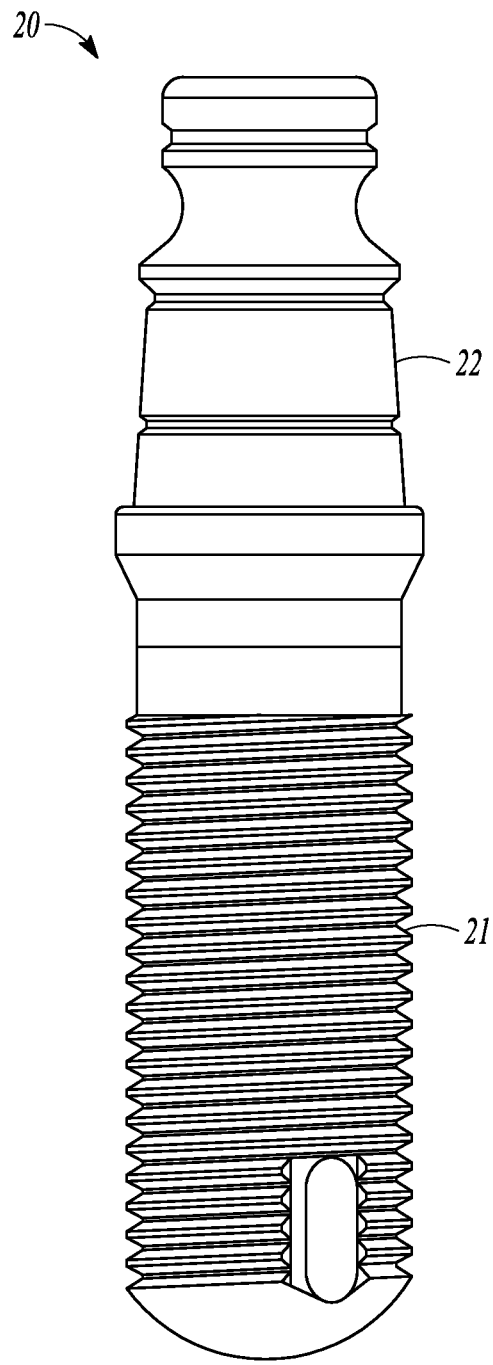
FIG. 3 is a perspective view of a dental prosthetic apparatus according to another aspect of the present disclosure.
Figure 4:
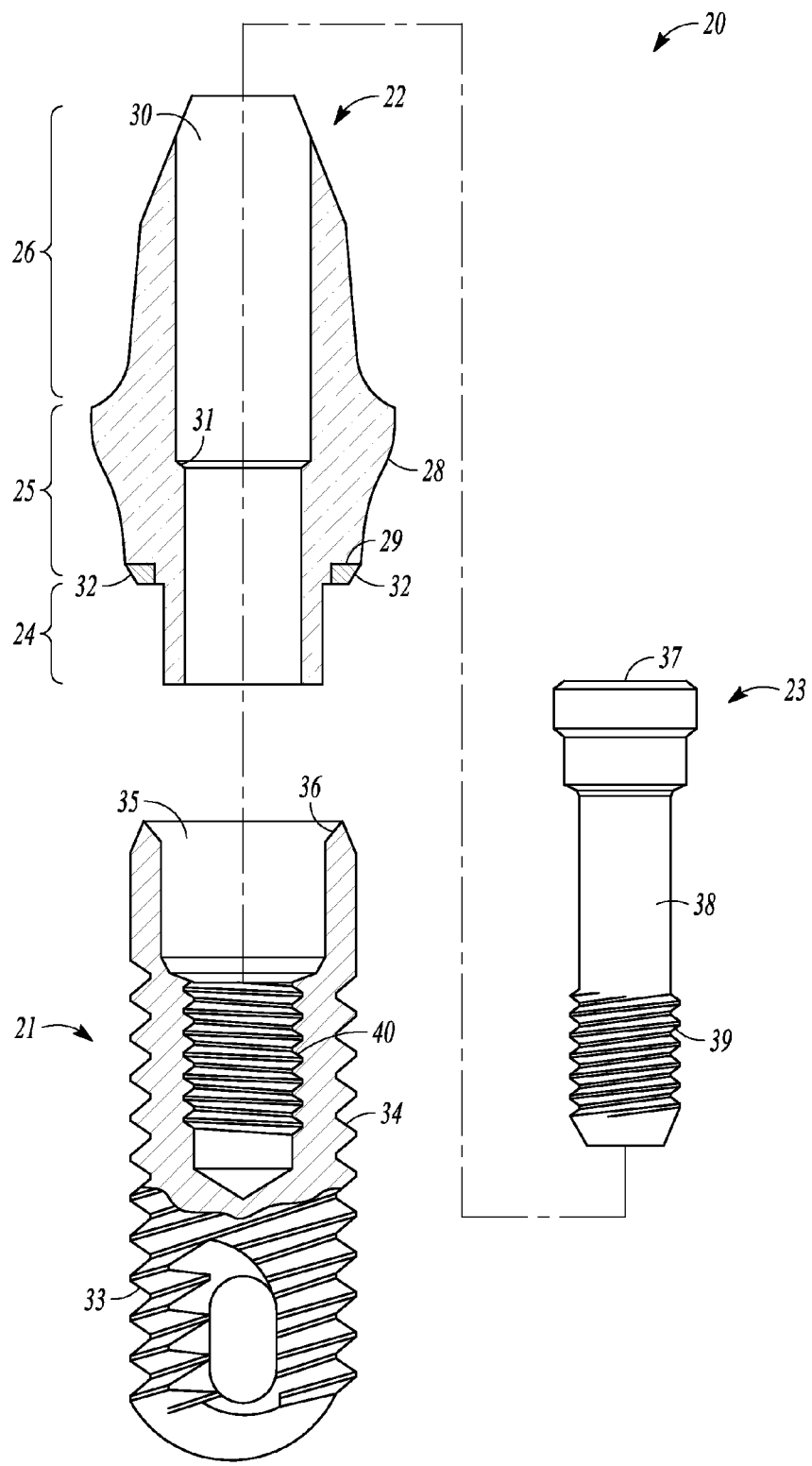
FIG. 4 is a partial cross-sectional and exploded view of a dental prosthetic apparatus in accordance with another embodiment of the present disclosure.
Figure 5:
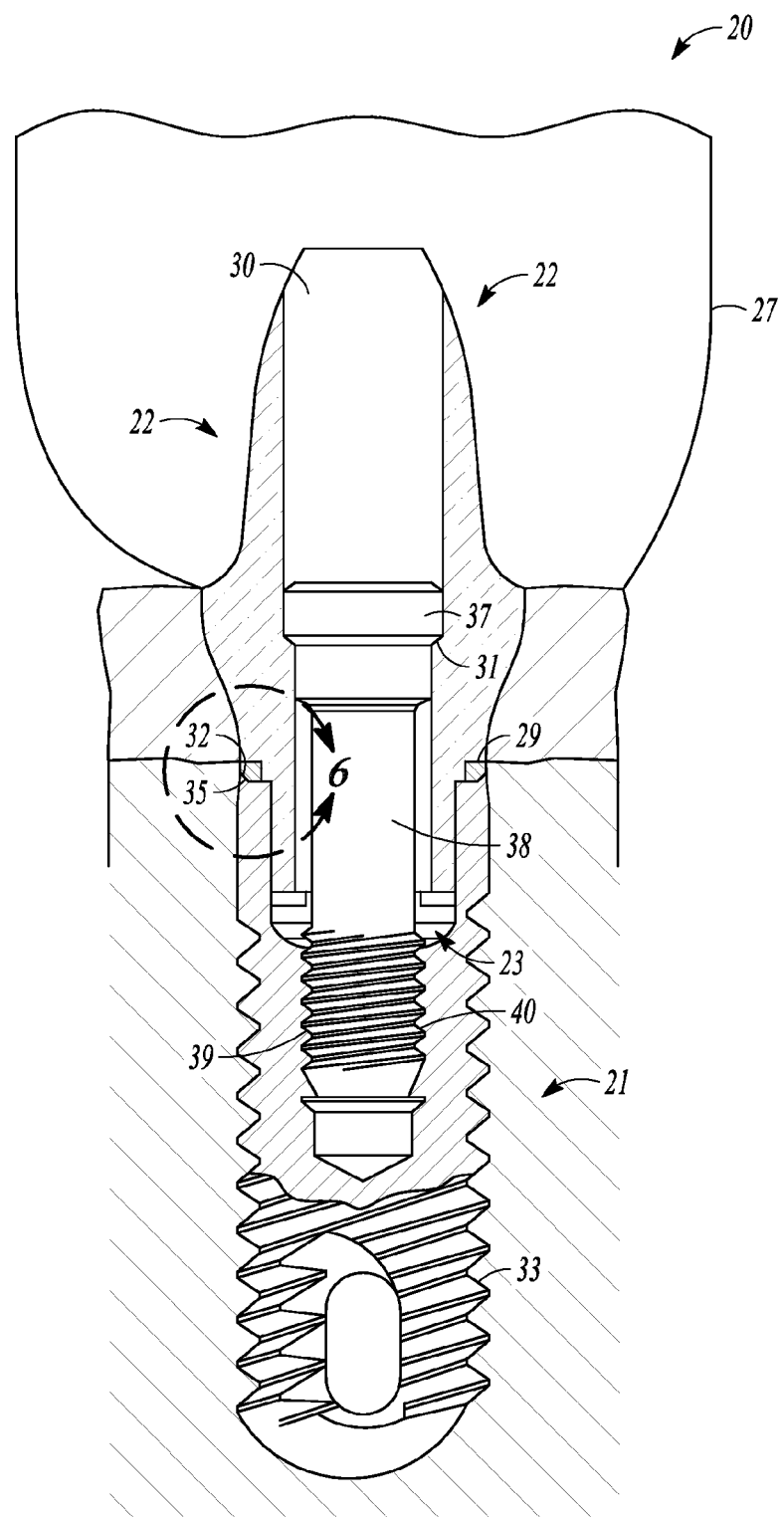
FIG. 5 is a partial cross-sectional view of the dental prosthetic apparatus in FIG. 4 in an implanted state, particularly illustrating the microgap between the anchoring and abutment members.

Turning now to FIGS. 3-5, a dental prosthetic apparatus 20 according to another aspect of the present disclosure is illustrated as generally including an anchoring member 21, an abutment member 22, and a connector 23 (FIGS. 4-5) interconnecting the anchoring and abutment members (21, 22) to provide a dental implant for a prosthetic tooth at an edentulous site in a patient's dentition where a natural tooth has been lost or damaged.

Referring to FIG. 4, the abutment member 22 generally includes a base portion 24 adapted to be mated with the anchoring member 21, a transgingival portion 25 adapted to extend through soft gingival tissue, and a supragingival portion 26 adapted to extend beyond the transgingival portion 25 to which a prosthetic tooth or crown 27 may be attached. The abutment member 22 generally includes a body 28 made of a suitable material, such as aluminum oxide, zirconium oxide, commercially pure titanium, or titanium alloy. As shown in FIGS. 4-5, the body 28 of the abutment member 22 defines a center bore 30. The bore 30 includes a step 31 for abutting engagement by the connector 23 to secure the abutment member 22 to the anchoring member 21, as described later in this disclosure.

The abutment member 22 further includes a collar 29 provided on the base portion 24 of the abutment member 22. The collar 29 may be made of a suitable biocompatible metal, such as titanium. The collar 29 may be attached to the base portion 24 of the abutment member 22 through a press-fit connection, an adhesive connection, a shrink-fit connection, or a brazed connection. As illustrated in FIG. 5, the collar 29 may include an exterior abutting surface 32 for abutting engagement with the anchoring member 21. The exterior abutting surface 32 of the collar 29 may be frusto-conical, annular, polygonal, other suitable shapes, or combinations thereof.

Referring to FIGS. 4-5, the anchoring member 21 generally includes a threaded body 33 adapted to be implanted into a jawbone of a patient according to known surgical techniques. To that end, the body 33 of the anchoring member 21 includes an exterior surface 34 for interacting with bone tissue to secure the anchoring member 21 to the jawbone, such as through osseointegration or other biological and/or mechanical interactions.

The body 33 also includes a center bore 35 in which the base portion 24 of the abutment member 22 is inserted. The center bore 35 further include an interior abutting surface 36 that is adapted to conform with the exterior abutting surface 32 of the collar 29 when the based portion 24 of the abutment member 22 is inserted into the center bore 35 of the anchoring member 21. The interior abutting surface 36 of the center bore 35 may be frusto-conical, annular, polygonal, other suitable shapes, or combinations thereof.

As illustrate in FIGS. 4-5, the connector 23 is provided in the dental prosthetic apparatus 20 for securing the abutment member 22 to the anchoring member 21. The connector 23 generally includes a head 37 and a shank 38 extending from the head 37 and terminating into a threaded tail 39. In use, the connector 23 is inserted through the center bore 30 of the abutment member 22, and the tail 39 of the connector 23 is threaded into an internally threaded region 40 of the center bore 35 of the anchoring member 21 until the head 37 of the connector 23 abuts the step 31 of the center bore 30 of the abutment member 22.

Figure 6:
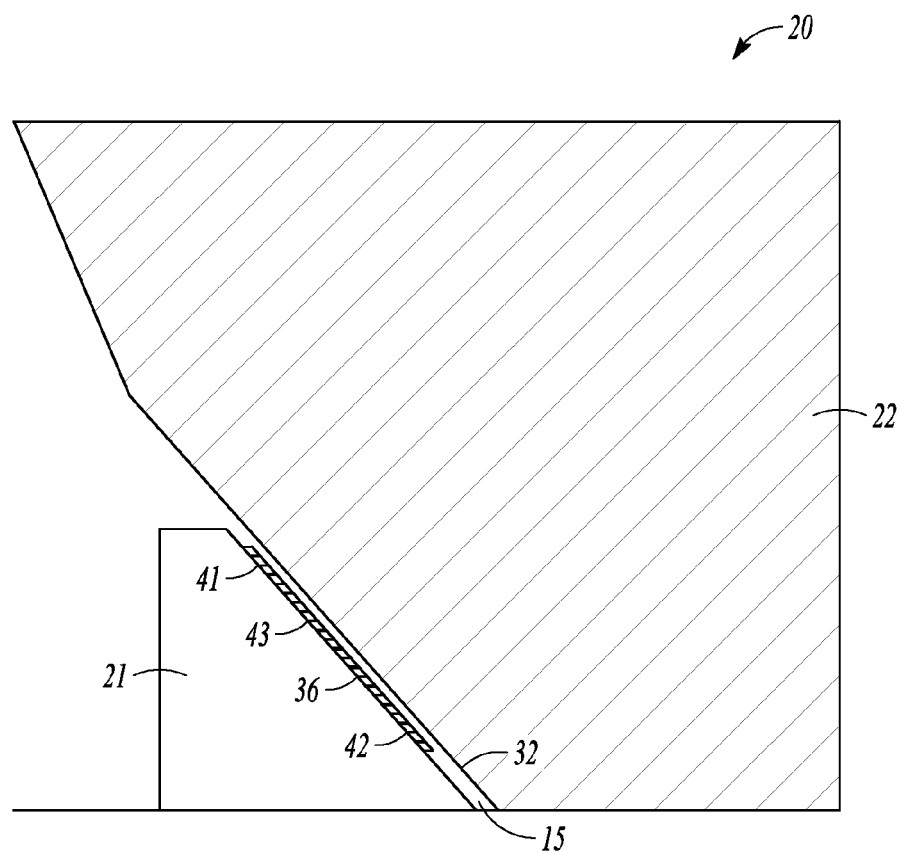
FIG. 6 is an enlarged view of the microgap area in FIG. 5, particularly illustrating the probiotic microorganisms retained in the microgap.

As illustrated in FIG. 6, the dental prosthetic apparatus 20 further includes at least one strain of probiotic microorganisms 41 retained between the interior abutting surface 36 of the anchoring member 21 and the exterior abutting surface 32 of the abutment member 22 prior to implantation of the dental prosthetic apparatus 20. Accordingly, the interior and exterior abutting surfaces (36, 32) and the microgap 15 therebetween may be essentially free of antimicrobial agents. The at least one strain of probiotic microorganisms 41 may be supported by a polymer matrix 42 to form a probiotic film 43 in some embodiments of the present disclosure. To that end, the probiotic microorganisms 41 may be impregnated in, coated on, or otherwise associated with the polymer matrix 42 prior to implantation of the dental prosthetic apparatus 20. It is to be understood that the use of with the polymer matrix 42 to carry the probiotic microorganisms 41 is a non-limiting embodiment of the present disclosure. In other embodiments the probiotic microorganism may be directly deposited on one or both of the mating interior and exterior abutting surfaces (36, 32). For example, the probiotic microorganisms 41 can be attached directly to the interior and exterior abutting surfaces (36, 32) via embedding in surface roughness, protein adhesion, culturing, or other techniques that do not require a polymer matrix.

As illustrated in FIG. 6, the polymer matrix 42 may be attached to at least one of the interior abutting surface 36 of the anchoring member 21 and exterior abutting surface 32 of the abutment member 22. In some embodiments, the polymer matrix 42 may be attached to both of the abutting surfaces (36, 32). The polymer matrix 42 may be attached to the abutting surfaces (36, 32) through adhesion, chemical bonding, thermal fusion, mechanical attachment or fixation mechanisms, etc. In some embodiments, the polymer matrix 42 may also be loosely disposed between the abutting surfaces (36, 32) without any attachment thereto. Furthermore, although only one polymer matrix 42 is shown in FIG. 6, the at least one strain of probiotic microorganisms 41 may be supported by more than one polymer matrix 42. For example, the dental prosthetic apparatus 20 may include two or more polymer matrices 42 either attached to one or both of the abutting surfaces (36, 32) or loosely disposed between the abutting surfaces (36, 32).

In some embodiments, the at least one strain of probiotic microorganisms 41 are uncolonized (e.g. dehydrated) prior to implantation and are capable of colonization in or on the polymer matrix 42, between the abutting surfaces (36, 32), and/or on the abutting surfaces (36, 32) upon rehydration through contact with saliva. In other embodiments, the at least one strain of probiotic microorganisms 41 are colonized (e.g. hydrated) in or on the polymer matrix 42, between the abutting surfaces (36, 32), and/or on the abutting surfaces (36, 32) prior to implantation of the dental prosthetic apparatus 20.

As used in the present disclosure, the term "probiotic microorganisms" broadly include bacteria, yeast or mold. Suitable probiotic microorganisms may be selected according to one or more particular properties. One of such properties is that the probiotic microorganisms display competitive exclusion of pathogenic organisms where the probiotic microorganisms are applied and colonized. Other properties may include, but not be limited to, adherence to surfaces, rate of colonization, sensitivity to antibiotics, antimicrobial activity, acid tolerance, and oxygen tolerance.

In light of the features and characteristics of the disclosed prosthetic apparatus, it is found that non-limiting examples of the genus of the probiotic microorganisms suitable for use in the prosthetic apparatus according to the present disclosure may include but are not limited to, *Lactobacillus, Lactococcus, Bifidobacteria, Streptococcus*, and combinations thereof. Moreover, non-limiting examples of the species of the probiotic microorganisms suitable for use in the prosthetic apparatus according to the present disclosure may include but are not limited to, *Lactobacillus rhamnosus, Lactobacillus acidolphilus, Lactobacillus reuteri, Lactobacillus casei, Lactobacillus paracasei, Lactobacillus delbrueckii, Lactococcus lactis, Lactobacillus gaseeri, Lactobacillus bulgaricus, Lactobacillus herbeticus, Lactobacillus salivarius, Lactobacillus plantarum, Bifidobacterium animalis, Bifidobacterium longum, Bifidobacterium breve, Bifidobacterium lactis, Streptococcus thermophilus, Streptococcus salivarius, Streptococcus mutans*, and combinations thereof.

Finally, non-limiting examples of the strain of the probiotic microorganisms suitable for use in the prosthetic apparatus according to the present disclosure may include, but are not limited to, *Lactococcus lactis* NCC2211, *Lactobacillus rhamnosus* GG, ATCC53103 (LGG), *Bifidobacterium longum* BB536, *Lactobacillus delbrueckii* subsp *Bulgaricus* 2038, *Streptococcus salivarius* subsp *Thermophilus* 1131, *Lactobacillus casei* Shirota, *Bifidobacterium breve* Yakult, *Bifidobacterium lactis* FK120, *Bifidobacterium lactis* LKM512, *Lactobacillus acidophilus* CK92, *Lactobacillus acidophilus* La5, *Lactobacillus herbeticus* CK60, *Lactobacillus casei* SBR1202, *Lactobacillus paracasei* F19, *Lactobacillus paracasei* F19, *Lactobacillus paracasei* DSMZ16671, *Lactobacillus gaseeri* SP, *Lactobacillus salivarius* W24, *Bifidobacterium* SP, *Lactobacillus casei* NY1301, *Lactobacillus* LC1, *Bifidobacterium lactis* Bb-12, *Lactobacillus reuteri* ATCC PTA 6475, *Lactobacillus lactis* NCC221, *Streptococcus thermophilus* NCC1561, *Streptococcus Salivarius* Mia, *Saccharomyces boulardii, Lactobacillus rhamnosus* GG, *Lactobacillus plantarum* 299v, *Lactobacillus reuteri* PTA 5289, *Lactobacillus reuteri* SD2112, and combinations thereof.

Without wishing to be bound by any particular theory, it is contemplated in the present disclosure that the probiotic microorganisms used in the dental prosthetic apparatus may have beneficial effects on the oral environment by controlling colonization of cariogenic streptococci, candida albicans, and other harmful microflora. Although the biochemical mechanism by which this occurs is not fully understood, it is contemplated that the probiotic microorganisms used in the present disclosure may provide beneficial effects by reducing bacterial adhesion, modulating the surrounding pH, and producing antibacterial agents.

For example, when introduced into the oral cavity, the disclosed probiotic microorganisms may reduce the number of bacteria or harmful biofilms on the dental prosthetic apparatus, may decrease gum bleeding, gingivitis, and plaque formation, may induce remission of chronic symptoms when incorporated into periodontal dressings, and may reduce pathogenic bacterial colonization in hydroxyapatite treated surfaces.

Thus, by placing the probiotic microorganisms between mating or abutting surfaces of a prosthetic apparatus, the microgap between the mating and abutting surfaces may be preemptively colonized with beneficial bacteria, rather than being merely sterilized and waiting for pathogenic organisms to later colonize. In some embodiment, the probiotic microorganisms may flourish to the degree that they may create a physical seal between the mating surfaces, further preventing pathogenic ingress.

Moreover, the association of probiotic microorganisms with the polymer matrix to form a probiotic film may provide benefit over basic cellular attachment through better resistance against the hostile environments, disinfectants, antibiotics, and immune responses. Such a matrix may also provide a robust delivery system for homo- or hetero-geneous probiotic microorganisms. Finally, the probiotic microorganisms according to the present disclosure may be provides as "inactive" (dehydrated) prior to implantation and ready for "activation" (rehydration) by blood or saliva after implantation.

While only certain embodiments have been set forth, alternative embodiments and various modifications will be apparent from the above descriptions to those skilled in the art. These and other alternatives are considered equivalents and within the spirit and scope of this disclosure.

What is claimed is:

1. A dental prosthetic apparatus, comprising:
   an implant member including a center bore and a first mating surface, the first mating surface extending from an outer surface of the implant member to a surface defining the center bore;
   an abutment member including a base, receivable in the center bore, and a second mating surface that conforms to the first mating surface, the second mating surface positioned coronal of the base;
   at least one strain of probiotic microorganisms retained between the first and second mating surfaces of the implant member and the abutment member, respectively; and
   a longitudinally extending connector, coaxial with the center bore and the base, configured to interconnect the first and second members, wherein the first and second mating surfaces are essentially free of antimicrobial agents.

2. The dental prosthetic apparatus of claim 1, wherein the at least one strain of probiotic microorganisms is supported by a polymeric matrix disposed between the first and second mating surfaces of the implant member and the abutment member, respectively.

3. The dental prosthetic apparatus of claim 2, wherein the polymeric matrix is attached to at least one of the first and second mating surfaces.

4. The dental prosthetic apparatus of claim 2, wherein the at least one strain of probiotic microorganisms is uncolonized in the polymer matrix.

5. The dental prosthetic apparatus of claim 4, wherein the at least one strain of probiotic microorganisms is capable of colonization in the polymer matrix upon contact with body fluid.

6. The dental prosthetic apparatus of claim 2, wherein the at least one strain of probiotic microorganisms is colonized in the polymer matrix.

7. The dental prosthetic apparatus of claim 1, wherein the first and second mating surfaces define a gap having a width of no more than 1000 micrometers.

8. The dental prosthetic apparatus of claim 1, wherein the at least one strain of probiotic microorganisms is selected from the genus group consisting of *Lactococcus, Lactobacillus, Bifidobacteria, Streptococcus*, and combinations thereof.

9. The dental prosthetic apparatus of claim 8, wherein the at least one strain of probiotic microorganisms is selected from the species group consisting of *Lactobacillus rhamnosus, Lactobacillus acidophilus, Lactobacillus reuteri, Lactobacillus casei, Lactobacillus paracasei, Lactobacillus delbrueckii, Lactococcus lactis, Lactobacillus gaseeri, Lactobacillus bulgaricus, Lactobacillus herbeticus, Lactobacillus salivarius, Lactobacillus plantarum, Bifidobacterium animalis, Bifidobacterium longum, Bifidobacterium breve, Bifidobacterium lactis, Streptococcus thermophilus, Streptococcus salivarius, Streptococcus mutans*, and combinations thereof.

10. The dental prosthetic apparatus of claim 9, wherein the at least one strain of probiotic microorganisms is selected from the strain group consisting of *Lactococcus lactis* NCC2211, *Lactobacillus rhamnosus* GG, ATCC53103 (LGG), *Bifidobacterium longum* BB536, *Lactobacillus delbrueckii* subsp *Bulgaricus* 2038, *Streptococcus salivarius* subsp *Thermophilus* 1131, *Lactobacillus casei* Shirota, *Bifidobacterium breve* Yakult, *Bifidobacterium lactis* FK120, *Bifidobacterium lactis* LKM512, *Lactobacillus acidophilus* CK92, *Lactobacillus acidophilus* La5, *Lactobacillus herbeticus* CK60, *Lactobacillus casei* SBR1202, *Lactobacillus paracasei* F19, *Lactobacillus paracasei* F19, *Lactobacillus paracasei* DSMZ16671, *Lactobacillus gaseeri* SP, *Lactobacillus salivarius* W24, *Bifidobacterium* SP, *Lactobacillus casei* NY1301, *Lactobacillus* LC1, *Bifidobacterium lactis* Bb-12, *Lactobacillus reuteri* ATCC PTA 6475, *Lactobacillus lactis* NCC221, *Streptococcus thermophilus* NCC 1561, *Streptococcus Salivarius* Mia, *Saccharomyces boulardii, Lactobacillus rhamnosus* GG, *Lactobacillus plantarum* 299v, *Lactobacillus reuteri* PTA 5289, *Lactobacillus reuteri* SD2112, and combinations thereof.

11. A dental prosthetic apparatus, comprising:
an anchoring member including a center bore and a first abutting surface, the first abutting surface extending, at an acute angle as measured relative to a plane defined by a coronal end of the anchoring member, from an outer surface of the anchoring member to a surface defining the center bore;
an abutment member including a base, matably received in the center bore of the anchoring member, and a second abutting surface that conforms to the first abutting surface of the anchoring member, the second abutting surface positioned coronal of the base; and
at least one strain of probiotic microorganisms retained between the second abutting surface of the abutment member and the first abutting surface of the anchoring member, wherein the first abutting and second abutting surfaces are essentially free of antimicrobial agents.

12. The dental prosthetic apparatus of claim 11, wherein the at least one strain of probiotic microorganisms is supported by a polymeric matrix disposed between the second abutting surface of the abutment member and the first abutting surface of the anchoring member.

13. The dental prosthetic apparatus of claim 12, wherein the polymeric matrix is attached to at least one of the second abutting surface of the abutment member and the first abutting surface of the anchoring member.

14. The dental prosthetic apparatus of claim 12, wherein the at least one strain of probiotic microorganisms is uncolonized in the polymer matrix and is capable of colonization in the polymer matrix upon contact with body fluid.

15. The dental prosthetic apparatus of claim 12, wherein the at least one strain of probiotic microorganisms is colonized in the polymer matrix.

\* \* \* \* \*